US00PP17434P2

(12) United States Plant Patent
Oliver

(10) Patent No.: US PP17,434 P2
(45) Date of Patent: Feb. 20, 2007

(54) ***HEUCHERA* PLANT NAMED 'MOONLIGHT'**

(50) Latin Name: *Heuchera×hybrida*
Varietal Denomination: Moonlight

(76) Inventor: Charles Oliver, 921 Scottdale-Dawson Rd., Scottdale, PA (US) 15683

( * ) Notice: Subject to any disclaimer, the term of this patent is extended or adjusted under 35 U.S.C. 154(b) by 35 days.

(21) Appl. No.: 11/151,827

(22) Filed: Jun. 14, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Heuchera* plant named 'Moonlight', characterized by its full, densely foliated and uniformly mounded plant habit; silver and purple bronze-colored foliage; numerous large pale green-colored flowers arranged on mostly erect panicles; and excellent garden performance.

2 Drawing Sheets

Botanical designation: *Heuchera×hybrida.*
Cultivar denomination: 'Moonlight'.

BACKGROUND OF THE INVENTION

The present invention relates to a new and distinct cultivar of *Heuchera* plant, botanically known as *Heuchera×hybrida* and hereinafter referred to by the name 'Moonlight'.

The new *Heuchera* is a product of a planned breeding program conducted by the Inventor in Scottdale, Pa. The objective of the breeding program is to create new *Heuchera* cultivars having good plant vigor, dense and uniform plant habit, and showy and attractive flower and leaf coloration.

The new *Heuchera* was discovered by the Inventor in a controlled environment in Scottdale, Pa., from seedling progeny from a cross-pollination made by the Inventor in May, 1999, of the *Heuchera×hybrida* cultivar Silver Maps, not patented, as the female, or seed, parent with an unnamed selection of *Heuchera alba,* not patented, as the male, or pollen, parent. The new *Heuchera* was selected by the Inventor in June, 2001. The selection of this plant was based on its desirable flower and foliage coloration.

Asexual reproduction of the new *Heuchera* by cuttings in a controlled environment in Scottdale, Pa., since October, 2001, has shown that the unique features of this new *Heuchera* are stable and reproduced true to type in successive generations.

SUMMARY OF THE INVENTION

The cultivar Moonlight has not been observed under all possible environmental conditions. The phenotype may vary somewhat with variations in environment such as temperature and light intensity, without, however, any variance in genotype.

The following traits have been repeatedly observed and are determined to be the unique characteristics of 'Moonlight'. These characteristics in combination distinguish 'Moonlight' as a new and distinct cultivar of *Heuchera:*

1. Full, densely foliated and uniformly mounded plant habit.
2. Silver and purple bronze-colored foliage.

3. Numerous large pale green-colored flowers arranged on mostly erect panicles.
4. Excellent garden performance.

Plants of the new *Heuchera* can be compared to plants of the female parent, the cultivar Silver Maps. In side-by-side comparisons conducted by the Inventor in Scottdale, Pa., plants of the new *Heuchera* differed from plants of the cultivar Silver Maps in the following characteristics:

1. Plants of the new *Heuchera* had larger leaves than plants of the cultivar Silver Maps.
2. Plants of the new *Heuchera* and the cultivar Silver Maps differed in leaf coloration.
3. Plants of the new *Heuchera* had shorter inflorescences than plants of the cultivar Silver Maps.
4. Plants of the new *Heuchera* had larger flowers than plants of the cultivar Silver Maps.
5. Plants of the new *Heuchera* and the cultivar Silver Maps differed in flower coloration.

Plants of the new *Heuchera* can be compared to plants of the male parent, the unnamed selection of *Heuchera×alba.* In side-by-side comparisons conducted by the Inventor in Scottdale, Pa., plants of the new *Heuchera* differed from plants of the male parent selection in the following characteristics:

1. Plants of the new *Heuchera* and the male parent selection differed in leaf coloration.
2. Plants of the new *Heuchera* had narrower inflorescences than plants of the male parent selection.
3. Plants of the new *Heuchera* had narrower flowers than plants of the male parent selection.

Plants of the new *Heuchera* can be compared to plants of the cultivar Silver Scrolls, disclosed in U.S. Plant Pat. No. 12,066. In side-by-side comparisons conducted by the Inventor in Scottdale, Pa., plants of the new *Heuchera* differed from plants of the cultivar Silver Scrolls in the following characteristics:

1. Plants of the new *Heuchera* had larger leaves than plants of the cultivar Silver Scrolls.
2. Plants of the new *Heuchera* and the cultivar Silver Scrolls differed in leaf coloration.
3. Plants of the new *Heuchera* had shorter and narrower inflorescences than plants of the cultivar Silver Scrolls.

4. Plants of the new *Heuchera* had larger flowers than plants of the cultivar Silver Scrolls.

BRIEF DESCRIPTION OF THE PHOTOGRAPHS

The accompanying colored photographs illustrate the overall appearance of the new *Heuchera,* showing the colors as true as it is reasonably possible to obtain in colored reproductions of this type. Colors in the photographs may differ slightly from the color values cited in the detailed botanical description which accurately describe the colors of the new *Heuchera.*

The photograph on the first sheet comprises a side perspective view of a typical flowering plant of 'Moonlight'.

The photograph on the second sheet is a close-up view of a typical inflorescence of 'Moonlight'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following detailed botanical description describe plants grown in Scottdale, Pa. in a glass-covered greenhouse and under cultural conditions which approximate commercial practice. Plants were grown as single plants in one-gallon containers and were about one year old when the photograph and description were taken. During the production of the plants, day temperatures ranged from 15 to 26° C. and night temperatures ranged from 5 to 15° C.

Botanical classification: *Heucherax×hybrida* cultivar Moonlight.

Parentage:

*Female, or seed, parent.*—*Heucherax×hybrida* cultivar Silver Maps, not patented.

*Male, or pollen, parent.*—Unnamed selection of *Heuchera alba,* not patented.

Propagation:

*Type.*—By cuttings.

*Time to initiate roots.*—Summer: About 15 days at 23° C. Winter: About 21 days at 17° C.

*Time to produce a rooted cutting.*—Summer: About 45 days at 23° C. Winter: About 60 days at 17° C.

*Root description.*—Fine, fibrous; white in color.

*Rooting habit.*—Freely branching.

Plant description:

*Appearance.*—Perennial; basal rosette plant habit with leaves developing from the base; densely foliated; full, mounded and uniform plant habit with upright panicles with pale green-colored flowers. Vigorous growth habit.

*Plant size.*—Height, soil level to top of foliar plane: About 15 to 20 cm. Height, soil level to top of panicles: About 40 to 45 cm. Diameter or spread: About 35 cm.

*Foliage description.*—Arrangement: Basal rosette, simple. Length: About 7.5 to 9 cm. Width: About 6.5 to 8 cm. Shape: Rounded cordate; seven-lobed. Apex: Broadly obtuse, lobed. Base: Auriculate. Margin: Crenate with ciliation. Texture, upper and lower surfaces: Slightly pubescent; slightly rough. Venation pattern: Palmate; reticulate. Color: Developing and fully expanded leaves, upper surface: 197A underlain with 183B with areas of 196B; venation, 197A underlain with 183B. Developing and fully expanded leaves, lower surface: 183B; venation, 183B. Petiole: Length: About 12 to 15 cm. Diameter: About 2 mm. Texture, upper and lower surfaces: Smooth. Color, upper and lower surfaces: 59B.

Flower description:

*Appearance/arrangement.*—Single campanulate flowers arranged on loose, narrow and mostly erect panicles; about eight to ten panicles develop during the flowering season each panicle with about 100 to 150 flowers and flower buds. Flowers face mostly outward to slightly downward. Flowering continuous. Flowers persistent. Flowers not fragrant.

*Time of flowering.*—Plants flower from May through June in Scottdale, Pa.; flowering continuous during this period.

*Inflorescence longevity.*—Individual inflorescences last about one week on the plant.

*Inflorescence size.*—Length: About 40 to 45 cm. Diameter: About 3.2 cm.

*Flower size.*—Diameter: About 6 mm. Depth (height): About 9 mm.

*Flower buds.*—Height: About 6 mm. Diameter: About 4 mm. Shape: Bulbous. Color, at stage of showing color: 151B; towards the base, shaded with 59B.

*Sepals.*—Quantity/arrangement: Five sepals; radially symmetrical and fused at base. Calyx length: About 7 mm. Calyx diameter: About 6 mm. Shape: Elongate. Apex: Obtuse. Margin: Entire. Texture, upper and lower surfaces: Pubescent. Color, upper surface: 150C. Color, lower surface: 150C; glandular hairs, 59B.

*Petals.*—Quantity/arrangement: Five minute petals; radially symmetrical. Length: About 5 mm. Width: About 1.7 mm. Shape: Spatulate. Apex: Acute. Margin: Serrate. Texture, upper and lower surfaces: Slightly pubescent. Color, upper and lower surfaces: Close to 155D.

*Flower bracts.*—Length: About 2 mm. Width: About 0.5 mm. Shape: Lanceolate. Apex: Acute. Margin: Serrate. Texture, upper and lower surfaces: Pubescent. Color, upper and lower surfaces: 59B.

*Peduncle.*—Strength: Strong. Aspect: Mostly erect. Length: About 30 cm. Diameter: About 2 mm. Texture: Pubescent. Color: 59B.

*Pedicels.*—Strength: Strong. Aspect: About 30° from vertical. Length: About 3 mm. Diameter: About 0.2 mm. Texture: Pubescent. Color: 151B shaded with 59B.

*Reproductive organs.*—Androecium: Stamen number: Five per flower. Anther shape: Oval. Anther length: About 1 mm. Anther width: About 0.6 mm. Anther color: 25A. Amount of pollen: Moderate. Pollen color: 25A. Gynoecium: Pistil number: Two per flower. Pistil length: About 5.5 mm. Stigma shape: Round. Stigma color: 157A. Style length: About 7 mm. Style color: 157A. Ovary color: 157A.

*Seed.*—Size: About 0.3 mm by 0.6 mm. Color: Close to 202A.

Disease/pest resistance: Resistance to pathogens and pests common to *Heuchera* has not been observed on plants grown under commercial conditions.

Weather/temperature tolerance: Plants of the new *Heuchera* have been observed to have excellent garden performance. Plants of the new *Heuchera* have demonstrated good tolerance to rain, wind, night temperatures as low as −35° C., and day temperatures as high as 45° C.

It is claimed:

1. A new and distinct cultivar of *Heuchera* plant named 'Moonlight', as illustrated and described.

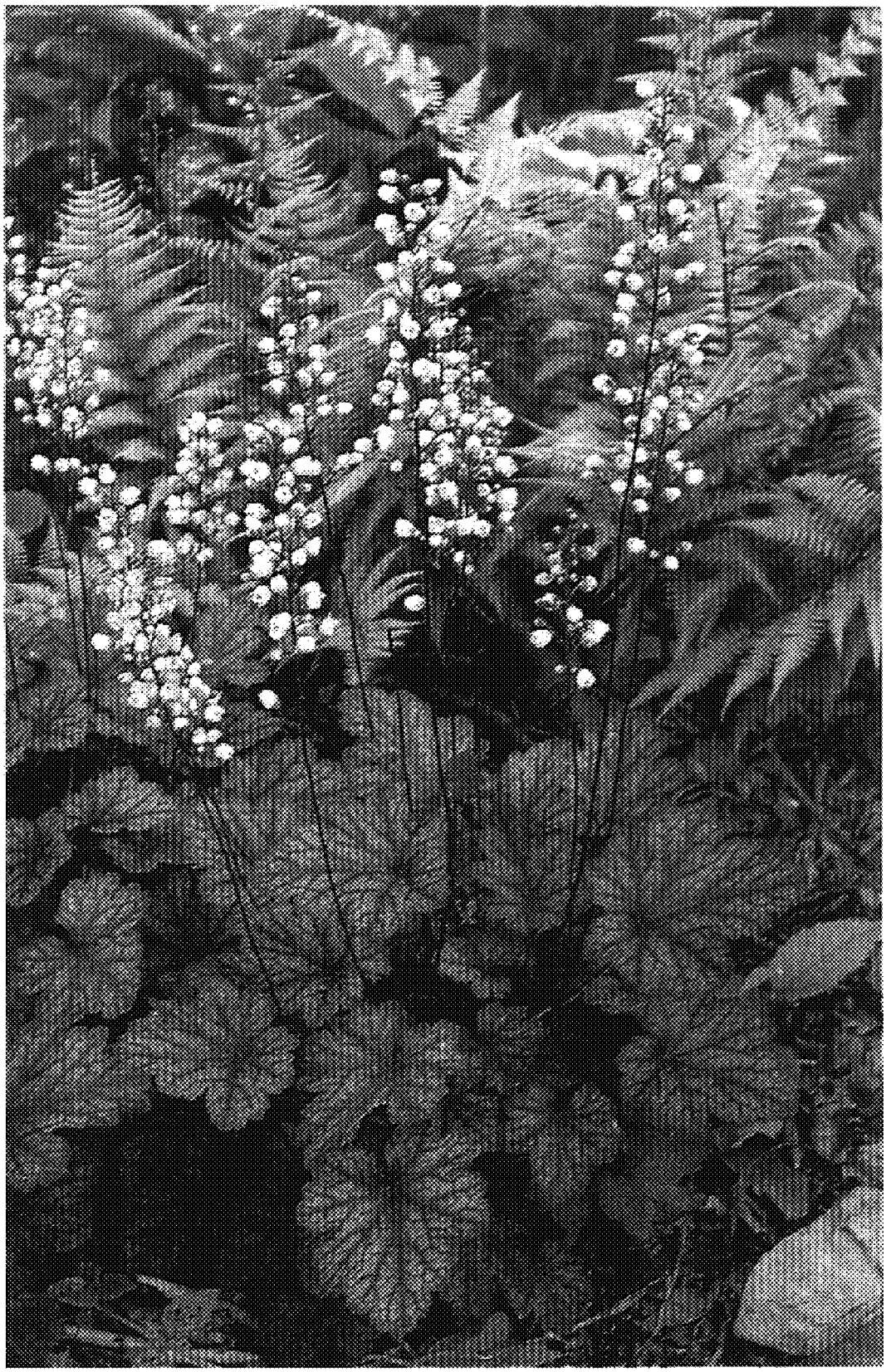

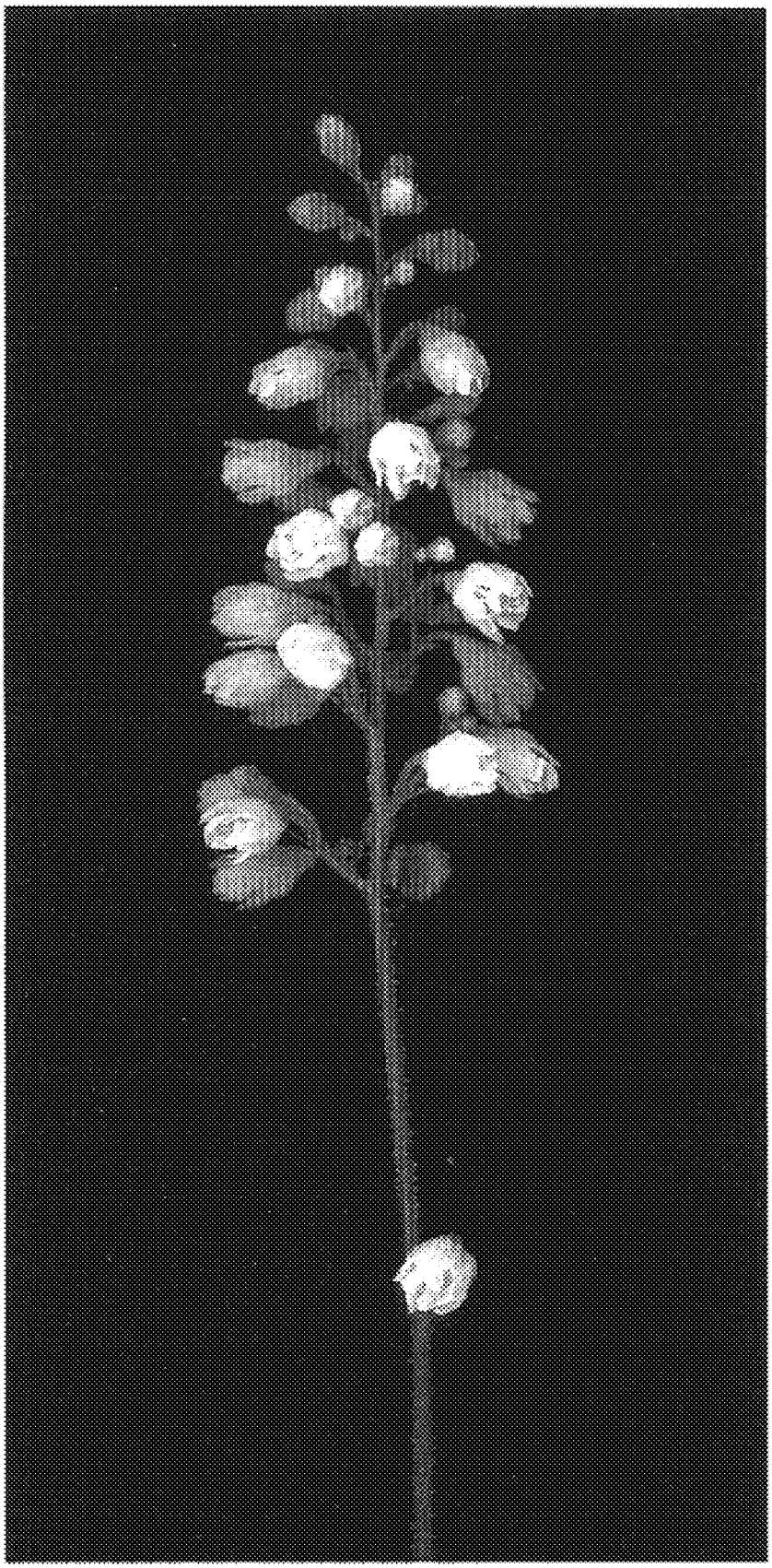

* * * * *